US011369517B2

(12) United States Patent
Hanft et al.

(10) Patent No.: US 11,369,517 B2
(45) Date of Patent: *Jun. 28, 2022

(54) DEVICE FOR MACHINING AN OBJECT BY APPLICATION OF LASER RADIATION

(71) Applicant: Carl Zeiss Meditec AG, Jena (DE)

(72) Inventors: Marco Hanft, Jena (DE); Dirk Muehlhoff, Jena (DE); Mario Gerlach, Glienicke-Nordbahn (DE); Elke Ebert, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 96 days.

This patent is subject to a terminal disclaimer.

(21) Appl. No.: 16/727,526

(22) Filed: Dec. 26, 2019

(65) Prior Publication Data

US 2020/0129329 A1 Apr. 30, 2020

Related U.S. Application Data

(63) Continuation of application No. 15/349,381, filed on Nov. 11, 2016, now Pat. No. 10,531,985, which is a
(Continued)

(30) Foreign Application Priority Data

Jul. 16, 2004 (DE) .......................... 102004034952.5
Jul. 11, 2005 (DE) .......................... 102005032946.2

(51) Int. Cl.
*A61F 9/008* (2006.01)
*A61B 3/14* (2006.01)
(Continued)

(52) U.S. Cl.
CPC .......... *A61F 9/0084* (2013.01); *A61B 3/0025* (2013.01); *A61B 3/0041* (2013.01);
(Continued)

(58) Field of Classification Search
CPC ..................................................... A61F 9/008
(Continued)

(56) References Cited

U.S. PATENT DOCUMENTS 4,865,441 A 9/1989 Reis
5,226,903 A 7/1993 Mizuno
(Continued)

FOREIGN PATENT DOCUMENTS

EP 0 815 801 A2 1/1998
JP 2000-56235 2/2000

OTHER PUBLICATIONS

Application and File History for U.S. Appl. No. 11/632,363, filed Jan. 12, 2007. Inventors: Marco Hanft et al.
(Continued)

*Primary Examiner* — Lynsey C Eiseman
(74) *Attorney, Agent, or Firm* — DeWitt LLP

(57) ABSTRACT

A device for machining an object by laser radiation, by photodisruption. The device includes an observation device for imaging the object and a laser scanning device by which the laser radiation is passed over a predetermined sector of the object for scanning the sector. The device includes the observation device with a first lens for imaging the object; the laser scanning device with a second lens, through which the laser radiation is guided, in which both lenses with regard to the dimension of the regions to be produced in the images and/or with regard to their focal intercept are different from each other. The device alternately images the respective region of the object in a first operating mode by the first lens and in a second operating mode by the second lens. It is thus possible to use in both operating modes a lens adapted to the intended imaging purpose.

20 Claims, 11 Drawing Sheets

Related U.S. Application Data continuation of application No. 11/632,363, filed as application No. PCT/EP2005/007519 on Jul. 12, 2005, now Pat. No. 9,498,844.

(51) Int. Cl.

| | |
|---|---|
| *B23K 26/03* | (2006.01) |
| *G02B 21/00* | (2006.01) |
| *G02B 21/22* | (2006.01) |
| *G02B 21/36* | (2006.01) |
| *A61B 3/00* | (2006.01) |
| *A61B 3/13* | (2006.01) |
| *G02B 21/02* | (2006.01) |
| *H04N 5/372* | (2011.01) |

(52) U.S. Cl.
CPC .............. *A61B 3/132* (2013.01); *A61B 3/145* (2013.01); *A61F 9/008* (2013.01); *B23K 26/03* (2013.01); *B23K 26/032* (2013.01); *G02B 21/0012* (2013.01); *G02B 21/025* (2013.01); *G02B 21/22* (2013.01); *G02B 21/361* (2013.01); *G02B 21/365* (2013.01); *H04N 5/372* (2013.01); *A61F 2009/00844* (2013.01); *A61F 2009/00872* (2013.01); *A61F 2009/00897* (2013.01)

(58) Field of Classification Search
USPC ......................................................... 606/4–6
See application file for complete search history.

(56) References Cited

U.S. PATENT DOCUMENTS

| | | |
|---|---|---|
| 5,506,725 A | 4/1996 | Koike et al. |
| 6,251,101 B1 | 6/2001 | Glockler |
| 6,292,214 B1 | 9/2001 | Sakano |
| 6,299,307 B1 | 10/2001 | Oltean et al. |
| 6,319,273 B1 | 11/2001 | Chen et al. |
| 6,485,413 B1 | 11/2002 | Boppart et al. |
| 6,530,918 B1 | 3/2003 | Ueno et al. |
| 7,288,106 B2 | 10/2007 | Heacock et al. |
| 2003/0053219 A1 | 3/2003 | Manzi |

OTHER PUBLICATIONS

Application and File History for U.S. Appl. No. 15/349,381, filed Nov. 11, 2016. Inventors: Marco Hanft et al.

| | Splitter 1 | | Splitter 2 | | Surgical Microscope | | | | Laser Scan Device | | | |
|---|---|---|---|---|---|---|---|---|---|---|---|---|
| | Trans. | Refl. | Trans. | Refl. | Trans. Channel 1 | Trans. Channel 2 | Trans. Channel 3 | TK2/ TK1 | Trans. Channel 1 | Trans. Channel 2 | Trans. Channel 3 | TK2/ TK1 |
| | | | | | | | | | | | | |
| T1 | 0,67 | 0,33 | 0,67 | 0,33 | 0,67 | 0,67 | 0,33 | 1,00 | 0,33 | 0,22 | 0,44 | 0,67 |
| T2 | 0,67 | 0,33 | 0,50 | 0,50 | 0,67 | 0,50 | 0,50 | 0,75 | 0,33 | 0,33 | 0,33 | 1,00 |
| T3 | 0,79 | 0,21 | 0,75 | 0,25 | 0,79 | 0,75 | 0,25 | 0,95 | 0,21 | 0,20 | 0,59 | 0,95 |

DEVICE FOR MACHINING AN OBJECT BY APPLICATION OF LASER RADIATION

CROSS-REFERENCE TO RELATED APPLICATIONS

This application is a continuation of application Ser. No. 15/349,381, filed Nov. 11, 2016, entitled "Device for Machining an Object by Application of Laser Radiation," which is a continuation of application Ser. No. 11/632,363, filed Jan. 12, 2007, entitled "Device for Machining an Object by Means of Laser Radiation,", now U.S. Pat. No. 9,498,844, issued Nov. 22, 2016, which is a national stage entry of PCT Application No. PCT/EP2005/007519, filed Jul. 12, 2005, which claims the benefit of German application DE102005032946.2 filed Jul. 11, 2005 and German application DE 102004034952.5 filed Jul. 16, 2004, each of which is hereby fully incorporated herein by reference.

TECHNICAL FIELD

The invention concerns a device for machining an object using laser radiation, including an observation device for imaging the object and a laser scan device used to guide the laser radiation energy scanning over a predetermined sector or inside of the object.

BACKGROUND

Prior art is known to include procedures and devices for machining objects using laser radiation that, for example, are used for shaping the cornea of the eye to correct poor vision. The required energy is brought into the tissue through pulsed laser radiation that is guided by scanning the sector of the lens from which tissue is to be removed.

More recent developments in connection with such ophthalmological surgical procedures for improving poor vision are using ultra-short pulse lasers to impart the energy and are known as fs-LASIK. The state of technology is described in R. Kurtz et al. *"Femtosecond Laser Corneal Refractive Surgery", Proc. SPIE* 3591, 209 (1999).

Here the laser radiation is focused on a focal point of a magnitude of just a few micrometers in the cornea. At the focal point a plasma is generated, which quickly vaporizes immediately adjacent tissue, causing a separation of the tissue at this location.

This interaction between the laser radiation and the tissue is called photo-disruption. Since the photo-disruption is limited to a microscopically small area, it is possible to create precise surgical cuts within the eye to achieve a locally restricted separation of the corneal tissue. Targeted rows of such separation zones allow macroscopic cuts and a predetermined partial corneal volume can be isolated. The removal of this partial volume achieves a desired change in the refraction of the cornea and thus a correction of the poor vision. In the following, the method based upon photo-disruption is referred to as fs-LASIK.

The procedure is designed so that prior to the fs-LASIK procedure, an observation device, for example a microscope, is used to inspect the object of the procedure and to determine the parameters of the treatment, such as the intensity of the laser radiation, pulse sequences, length and location of the cuts, etc. Following this, the procedure is carried out using the laser scan device.

Usually, the results of the procedure are evaluated again with the help of the observation device. Following this, post-surgical steps are carried out, such as the removal of the excised volume and the wound care.

SUMMARY

In order to make the manipulation and the sequence of the individual procedural steps as easy and efficient as possible, it is desirable to combine the observation device and the laser scan device in such a manner that the operator is able to focus in the eyepieces of the observation device throughout, from the preparation, during the procedure and the post-surgical evaluation.

However, the combination of observation device and laser scan device poses problems, because an image must be created first for the preparation, which allows the evaluation of the object for the subsequent treatment and to select the sector on the surface or within the object to be worked on. It is desirable to image a sector of the object that is significantly larger than the sector to be treated. Besides, the object frequently is subject to manipulations with instruments during the observation while using the observation device, which requires sufficient distance between the lens of the observation device and the object.

To make this possible, an observation device with an imaging system is used that has a focal intercept of >100 mm, to allow for images of sufficiently large sectors of the object and enough space for manipulations with instruments above the object, due to the distance between the lens and the object.

During the treatment mode, however, it is necessary to keep the distance small between the object and the lens through which the laser radiation is aimed at the object, so that it can be designed as a compact device, despite the relatively large aperture and the large field, and to allow the bridging of the distance between the lens and the object with a contact glass, used to fix the object, particularly if this object is an eye.

In order to do justice to the different, in some ways contradictory demands on the optical systems for the preparation mode on one hand and the treatment mode on the other, devices have been developed that contain an imaging system with variable focal intercept. As an example, such an imaging system has been described in US 2003/005319 A.

This imaging system has a relatively large focal intercept that, for the reasons stated above, is used during the preparatory and the evaluative modes. During the treatment mode, however, the focal intercept is shortened through the removal of optical elements from the optical path.

The negative aspects with this process and such an imaging system are primarily that during the preparatory and the evaluative modes the distance between the lens and the object still is not large enough, that no stereoscopic observation is possible and that the final lens, the one closest to the object, must have a very large diameter.

With a desirable focal intercept of e.g. 200 mm, the diameter of the final lens, the one closest to the object, would have to be approximately 45 mm. For anatomical reasons, however, such a diameter would makes it more difficult to bring the lens closer to the object, because with such dimensions the lens could collide with the patient's nose or forehead during eye surgery.

Embodiments of the invention include a device of the kind described above in which the sector to be treated is imaged in a way that is ergonomically improved for observation during the preparatory, the evaluative as well as during the treatment mode.

Example embodiments of the invention include a device for treating an object using laser radiation, largely consisting of:

An observation device with a first lens for imaging the object and

A laser scan device with a second lens through which the laser radiation, scanning, is guided across a sector of the object that is to be treated, whereby The two lenses are different from each other in terms of the size of the images depicted and/or in terms of their focal intercept and Means are provided for alternating images of the respective sectors of the object in a first operating mode through the first lens and, in a second operating mode, through the second lens.

Thereby, many disadvantages of the state of prior art are removed, because now it is possible to use a separate lens during the two operating modes that are matched to the respective imaging lens, namely during the first operating mode, referred to below as preparatory and evaluative mode, an optical imaging system with large focal intercept for preferred stereoscopic imaging of a sector of the object that is at least as large as the sector to be treated and, on the other hand, for a second treatment mode, referred to below as treatment mode, an optical imaging system with small focal intercept, which can be brought close to the object without interference and is well suited for scanning the laser radiation as well as imaging the treated sector during the treatment.

And example embodiment of a device according to the invention is fashioned with a positioning feature, making it possible to adjust the position of the object relative to the two lenses, whereby the object would be in focus through the first lens during the preparatory and evaluative modes and in focus through the second lens during the treatment mode.

This means that there is a sufficiently large manipulation distance between the lens and the object during the preparation, while the distance is clearly shortened in the other position.

Consequently, a significant idea according to example embodiments of the invention is combining the laser scan device and the observation device by replacing the lens of the observation device during treatment with the lens of the laser scan device, whereby the scan function of the lens of the laser scan device remains available, but it is utilized for additional observation.

To make this possible, the laser scan device has a decoupling lens in its optic path for light coming from the object during treatment, passing through the lens of the laser scan device, and there is a coupling lens in the optic path of the observation device that corresponds with the decoupling lens, so that during the treatment mode the lens of the laser scan device is used instead of the lens of the observation device that is used during the preparatory and evaluative modes.

There are optic and/or opto-electronic modules provided to transmit light from the decoupling to the coupling lens. It is advantageous if there is a select logic shutter provided in the path from the lens of the observation device to the coupling lens that can be used to block light coming from the unused lens of the observation device during the treatment mode.

In addition, there should be a shutter between the lens of the laser scan device and the coupling lens that blocks the light coming from the unused lens of the laser scan device during the preparatory and evaluative modes.

That way, an undesirable effect on the image by the wrong light is avoided during each respective operating mode. In an embodiment of the device according to the invention, the observation device is fashioned as a stereoscopic microscope and fundamentally includes:

The stereoscopic microscopic lens as the first lens,

Two separate imaging paths, making a stereoscopic image possible,

In each of the two separate optical paths, there is a magnification adjuster to preset different image scales, a tube lens system and an eyepiece, and A coupling lens.

Fundamentally, the coupling lens can include one or of two radiation splitters that are fashioned as radiation cube splitters or as radiation plate splitters, designed in such a fashion that light can be coupled or uncoupled in two directions respectively. This way it is possible to reflect the image into the imaging radiation path for visual observation as well as a partial decoupling of light for an additional observation device, e.g. a CCD camera.

In addition to its straightforward observation function, a CCD camera or another imaging device offers a basis for additional functions. For example, the images acquired in this fashion could support an adjustment process for the treatment mode. With the objective of creating a control loop, a CCD camera combined with a computer and a suitable manipulator would constitute a significant module.

An example coupling lens includes of two radiation splitters, each radiation splitter being assigned to one of the two imaging radiation paths and located between the magnification changer and the tube lens system. The brightness of the images can be varied by selecting the splitting ratio (ratio transmission/reflection) at the splitter layers of the radiation splitters.

It is recommend to install a shutter between the two radiation splitters in order to avoid a mutually interfering effect on the two imaging radiation paths due to the coupled light.

Of course, the scope of the invention also includes the provision of an optical observation device for monoscopic observation instead of the stereoscopic device.

Optical modules consisting of lenses, prisms, radiation deflecting elements and/or fiber-optics light transmitting devices can be used to transmit the light from the laser scan device to the observation device.

The light emerging from the object and passing through the lens of the laser scan device is transmitted to the observation device and coupled into the imaging radiation paths by means of the coupling lens.

The specific design can include basically the following optical modules for transmitting the light from the laser scan device to the observation device:

A group of lenses with a field lens downstream to generate an intermediate image from the pencil of light rays coming from the second lens, namely the lens of the laser scan device, A group of lenses for showing the intermediate image in at least one of the two imaging radiation paths of the observation device, and Optical elements to deflect and/or fold the radiation bundle.

In addition, an optical zoom system for varying the focal length, respectively the imaging scale of the intermediate image, can be located in the transmission path of the light from the laser scan device to the observation device, which consists for example of two lenses and lens groups that can be varied in their position relative to each other.

This gives the operator the opportunity to display the sector to be treated and simultaneously to observe it as a larger or smaller image.

It is further within the scope of the invention to provide opto-electronic modules for transmitting the light from the laser scan device to the observation device. For example, during the treatment mode the image of the object can be sent to an opto-electronic camera by means of the second lens, i.e. the lens of the laser scan device, the camera consisting largely of a video lens and a CCD receiver. Downstream from the camera are an image signal processor device and an imaging device; and there are means to couple the image shown on the imaging device into at least one of the two imaging radiation paths of the observation device, so that this way during the treatment mode the sector to be treated can be viewed through the eyepieces, respectively the eyepiece of the observation device as well.

An advantageous choice of an image display device would be an LC display.

For the transmission of the light from the laser scan device to the observation device, it is also imaginable to utilize optical as well as opto-electronic modules in combination or as exchangeable options.

In yet another embodiment of the invention, the device according to the invention is supplemented by an arrangement that makes it possible to determine the process parameters for the treatment, to determine data characterizing the properties of the material the object is made of and to register measuring data, which provide information on the expanse of the object or the sector to be treated.

In this context, additional means of projecting the information gathered into one or both radiation paths of the observation device, so that the operating personnel is able to observe through the eyepiece, respectively the eyepieces, during the treatment mode the sector to be treated and, at the same time, receives also the information about process parameters, dimensions and/or properties of the material.

In this context, there is another embodiment, where the observation device is fashioned as a stereoscopic Greenough-type microscope. With this microscope, each of the two stereoscopic imaging radiation paths contains a lens and, consequently, there is an opportunity to locate the device for determining information concerning process parameters, object dimensions or properties of the material within the space between the two lenses.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

The invention will be explained in more detail below through examples of embodiments. The respective drawings are showing

Figure 1:
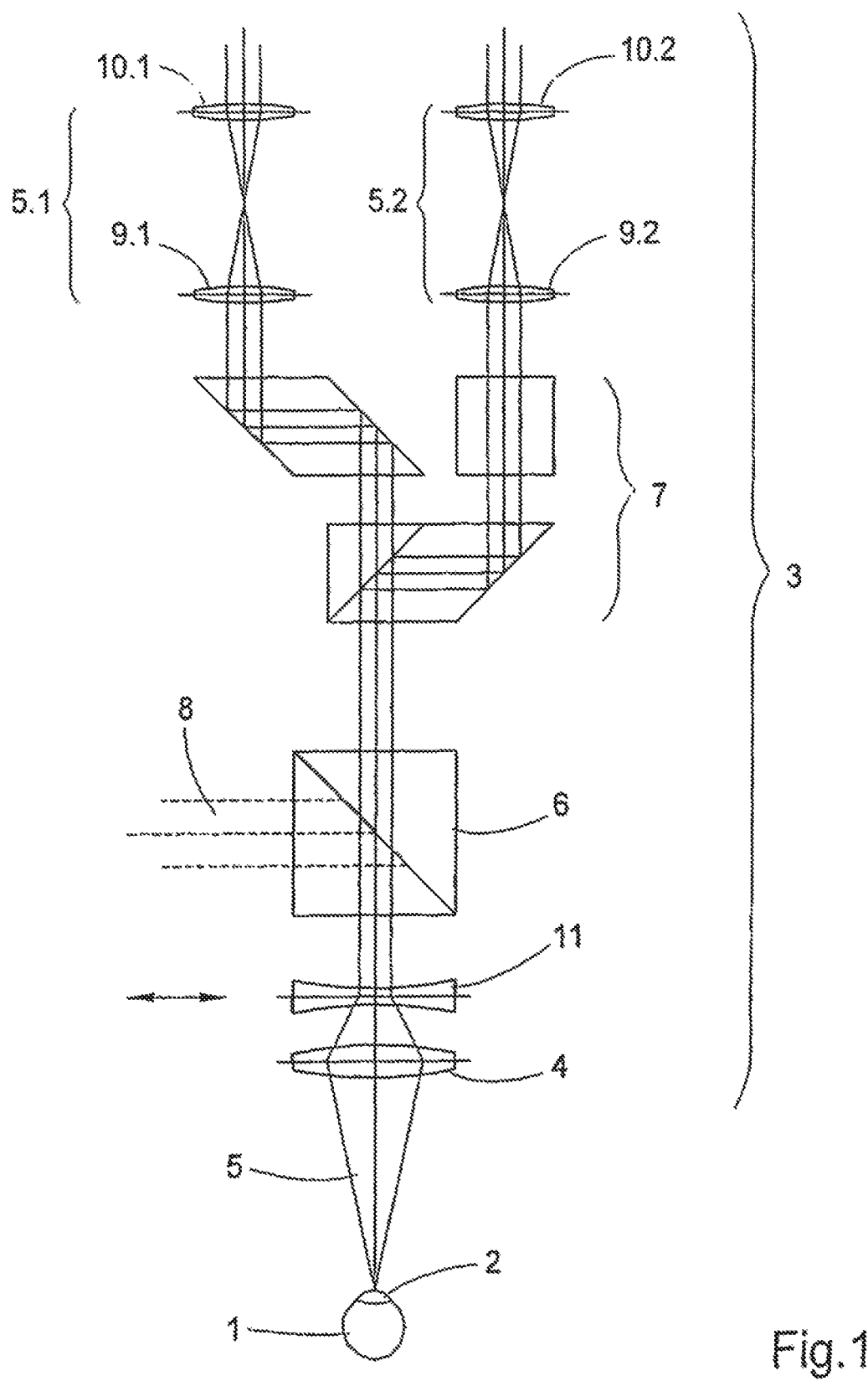
FIG. 1 is a schematic illustration of a device for treating an object using laser radiation according to the state of technology during the preparatory mode.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIG. 1 shows the most important modules of a device for treating an object 1 using fs-LASIK, as it is known by the state of technology.

Object 1 is the eye of a patient, in which a sector 2 is to be treated using photo-disruption, which can be below the surface or adjacent to the surface.

The treatment will be carried out using a laser source, which generates radiation with ultra-short pulses and where a laser scan device is placed downstream. Such devices are known from the bibliography above and from other documentations; this makes a detailed explanation of the process of photo-disruption unnecessary at this time.

The device according to the state of technology is shown in FIG. 1 during the mode of preparation for treatment and can be utilized in this configuration also for the evaluation of the results following the treatment.

An observation device 3, for example a microscope, is used first prior to the treatment procedure to image a sector of the object 1 in higher or lesser magnification, covering the sector 2, which is intended for treatment, so that the operator has the opportunity to locally narrow down sector 2 and to preset the treatment parameters, such as radiation intensity, duration of radiation, pulse sequence and length and so on.

The observation device 3 shows lens 4, through which the light coming from object 1 passes in a radiation path 5.

Downstream from the lens 4 are a radiation splitter 6 and a splitting system 7. The laser radiation 8 used for treatment can be coupled via the radiation splitter 6; the splitter system 7 is used to split the radiation path 5 into two partial radiation paths 5.1 and 5.2. Tube lenses 9.1 and 9.2 and eyepieces 10.1 and 10.2 are located in the two partial radiation paths 5.1 and 5.2. Using a swing-in/swing-away lens group 11 in radiation path 5, the focal intercept of the optical system, consisting of the lens 4 and the lens group 11, can be changed, as has been described in US 2003/0053219 A1. If the lens group 11 is swung into radiation path 5, as shown in FIG. 1, object 1 is shown with a focal intercept of, for example, 100 mm. This offers the advantage that, first of all, large areas of object 1, to be treated, can be shown and observed and, secondly, there will be space for manipulation with instruments between object 1 and lens 4.

The laser radiation source and the laser scan device are not in use during the mode of preparation for treatment, as shown in FIG. 1. To make this more obvious, active radiation paths are depicted in FIG. 1 and the following drawings as drawn-out lines and currently unused radiations paths as interrupted lines.

Figure 2:
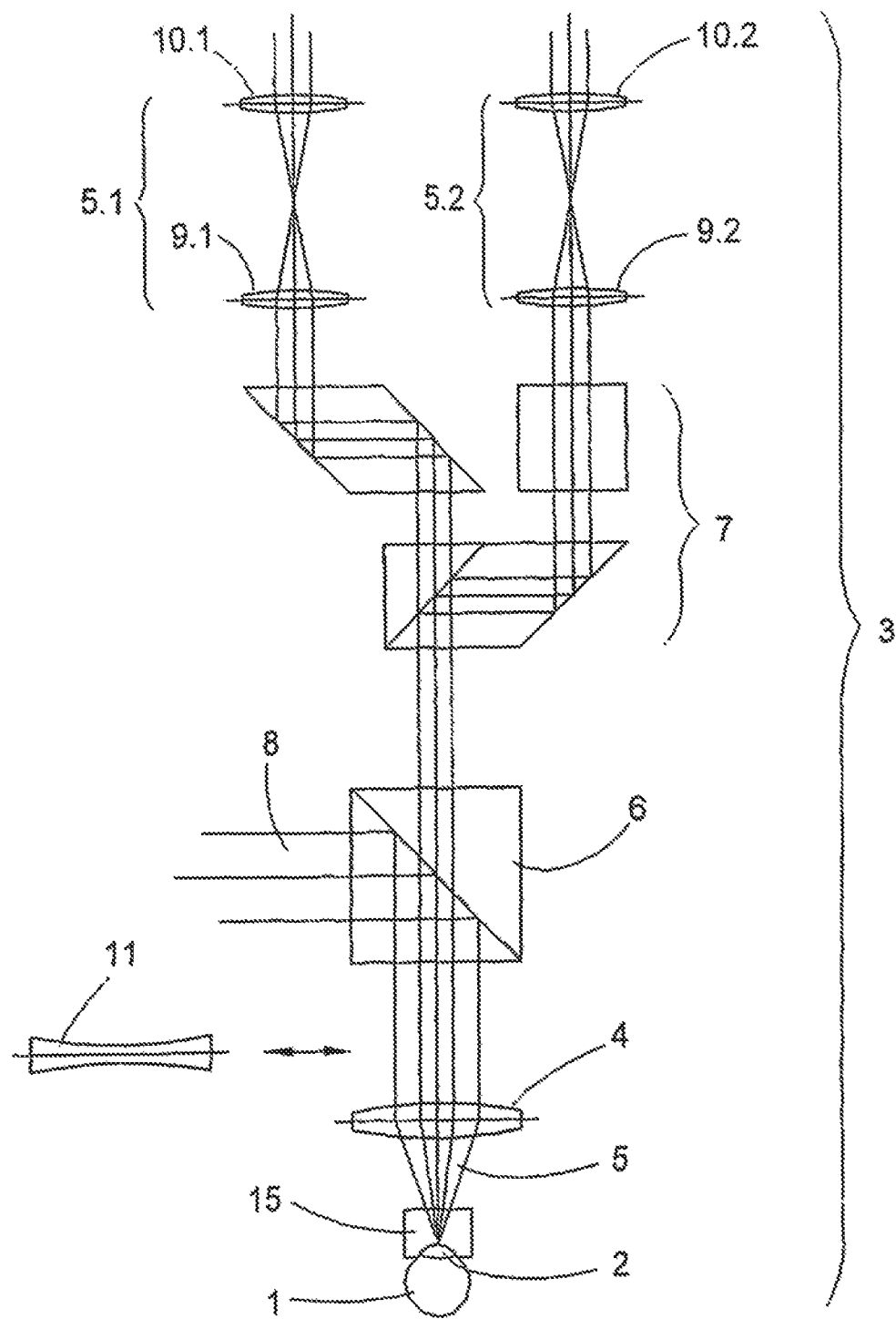
FIG. 2 is a schematic illustration of the device according to FIG. 1 during the treatment mode.

When the preparation for the treatment procedure has been completed, the device is changed to the treatment mode, as shown in FIG. 2.

To accomplish this change, lens group 11 is removed from radiation path 5, which reduces the focal intercept of the imaging optics. The lesser focal intercept is required for the treatment mode, to keep the focal distance between lens 4 and the object 1 close, so that the space no longer needed for manipulation with instruments can be bridged with a contact glass, required for fixing object 1.

Subsequently, the laser source and the laser scan device are started up, the laser radiation 8 is coupled via the radiation splitter 6 into the radiation path 5, aimed through the lens 4 at the object 1 and moved in a scanning fashion across the selected sector 2, where the photo-disruption takes place. The sector 2 and the course of the treatment procedure are visualized by means of the observation device 3.

A significant disadvantage of the state of technology described here is the fact, that the observation is limited to a monoscopic image.

To make it possible that just the same tube view can be used (eyepieces 20.1, 20.2 and tube lens systems 19.1 and 19.2), that a stereoscopic observation is possible during the preparatory mode as well as the condition met that imaging is done with a large focal intersect during the preparatory mode (and also during the evaluative mode) and during the treatment mode with a small focal intercept, the state of technology of the device according to the invention has been further developed, as is shown in FIG. 1 and FIG. 2, as is explained below in FIG. 3 through FIG. 8.

Figure 3:
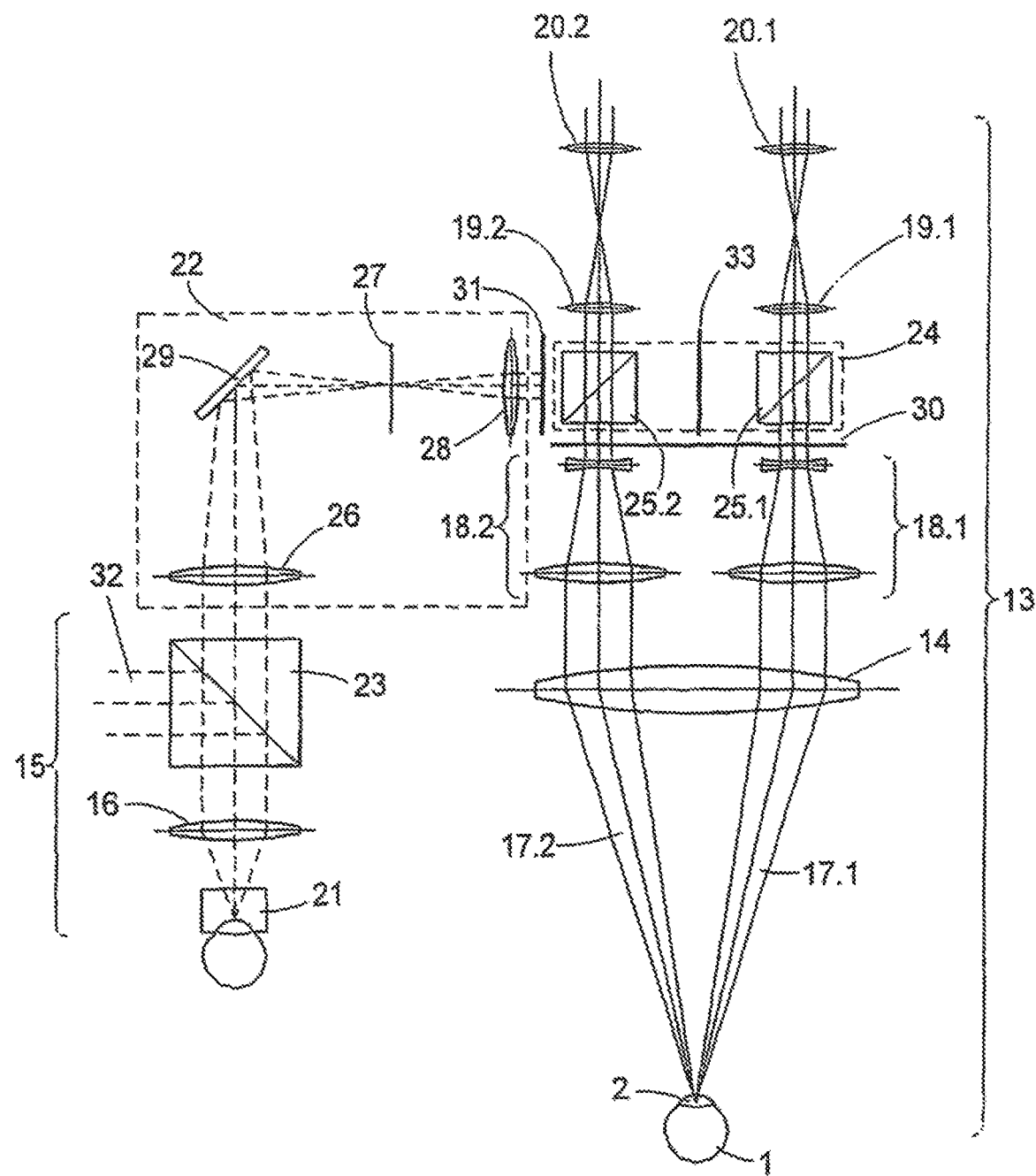
FIG. 3 is a schematic illustration of the device, according to the invention, for treating an object with laser radiation during the preparatory and evaluative modes, equipped with optical modules for decoupling light from the laser scan device and for coupling it into the imaging radiation paths of an observation device fashioned as a stereoscopic microscope.

As shown in FIG. 3 in principle, the device according to the invention includes an observation device 13 with a first lens 14 and a laser scan device 15 with a second lens 16. The observation device is fashioned as a stereoscopic microscope, having a magnification changer each, 18.1 and 18.2 in two radiation paths 17.1 and 17.2, a tube lens system 19.1 and 19.2 as well as an eyepiece 20.1 and 20.2.

The operator is able to view a smaller or larger area of the object 1 through the eyepieces 20.1 and 20.2, depending upon the adjustment of the image scale using the magnification changer, 18.1 and 18.2, then select from this area the sector 2 to be treated and determine the parameters, based upon his experience and knowledge in judging the situation.

As has been suggested in FIG. 3, the lens 14 has a relatively large focal intercept, for example, larger than 100 mm.

The lens 16 of the laser scan device 15, on the other hand, is designed with a significantly smaller focal intercept, for example 5 mm, so that the diameter of this lens can be fashioned sufficiently small and the distance between object 1 and lens 16 is small enough to be bridged with a contact glass 21.

According to an embodiment of the invention, the observation device 13 and the laser scan device 15 are connected by a coupler 22 that serves to transmit the light coming from object 1, passing through lens 16, to the observation device 13.

For decoupling the light to be transmitted from the laser scan device 15, it is equipped with a decoupling device 23 that can be fashioned as a radiation splitter.

Corresponding to this, there is a coupling lens 24 provided in the observation device 13, which is for example located between the magnification changers 18.1 and 18.2 and the tube lens systems 19.1 and 19.2. The coupling lens 24, for example, is also fashioned in form of radiation splitters, whereby one radiation splitter 25.1 is allocated to imaging radiation path 17.1 and an additional radiation splitter 25.2 to the imaging radiation path 17.2.

The coupling device 22 can be fashioned in several variants. In the variant depicted in FIG. 3, the coupling device 22 includes a group of lenses 26 to generate an intermediate image 27 and a group of lenses 28 for imaging this intermediate image 27 in the imaging radiation paths 17.1 and 17.2. A deflection element 29 serves to change the direction of the radiation path between the lens group 26 and lens group 28.

As can be seen in FIG. 3 as well, there is a shutter 30 in the path of the light of the imaging radiation paths 17.1 and 17.2 and there is a shutter 31 provided in the path of the light between the laser scan device 15 and the observation device 13, which can both be controlled alternately, once to block the path of the light through the lens 14 to the eyepieces 20.1 and 20.2 (shutter 30) or to block the path of the light from the lens 16 to the eyepieces 20.1 and 20.2.

FIG. 3 shows the device according to the invention during the preparatory and the evaluative modes. The object 1 is in focus of lens 14, the shutter 30 is open and the operator can observe the object 1 through the eyepieces 20.1 and 20.2 and prepare the treatment procedure as described above.

To avoid crosstalk during this mode of operation, respectively an undesirable mutual interaction of the imaging radiation paths 17.1, 17.2, there is another shutter 33 provided between the radiation splitters 25.1 and 25.2 that can be used to block the light, if needed.

The laser radiation source and the laser scan device (not shown in FIG. 1) are not in operation, as documented by the interrupted lines of the radiation path in the laser scan device 15. The shutter 31 is closed, so that no light is transmitted from the laser scan device 15 via the optical coupling device 22 to the imaging radiation paths 17.1, 17.2 of the observation device 13.

Figure 4:
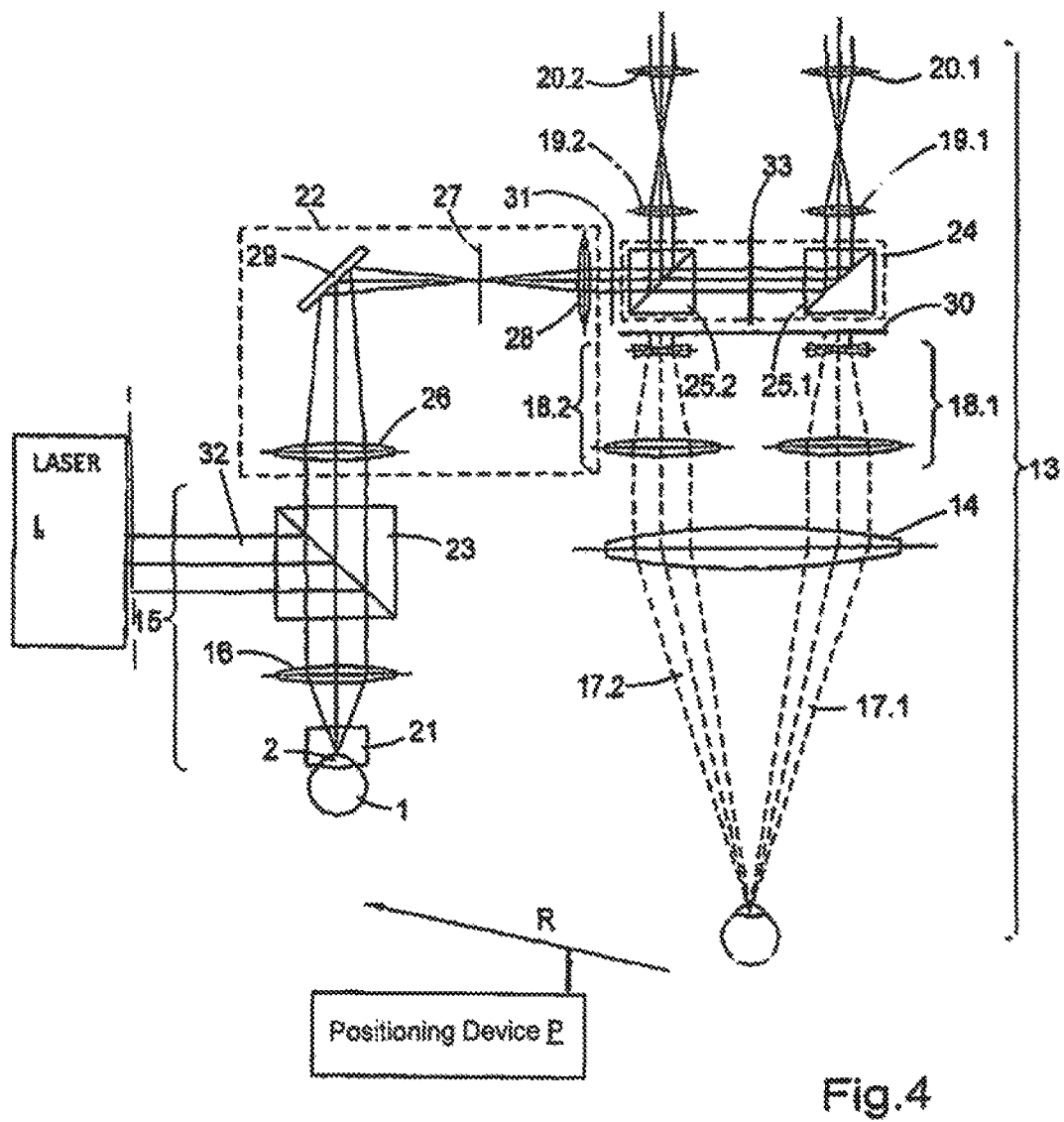
FIG. 4 is a schematic illustration of the device, according to the invention, as per FIG. 3 during the treatment mode.

When the preparations for the treatment procedure have been completed and the treatment parameters have been determined, the device is switched from the preparatory and evaluative modes to the treatment mode, as shown in FIG. 4.

To do so, the object 1 is shifted relative to the lenses 14, 16 in the direction R, so that the object 1 is no longer in focus of lens 14 but rather in focus of lens 16. This shifting can be accomplished in such a manner that the device is moved relative to the object 1, but preferably the object 1 (respectively the patient) is moved relative to the device, respectively the lenses 14, 16.

To accomplish this, a positioning device may be provided, where in a first end position the object 1 is in focus of lens 14 and, in a second end position, the object 1 is in focus of lens 16. The positioning device is not shown. It can be equipped with a movable table that is connected to a drive system. The arrival at the end position is monitored by appropriately positioned sensors that are coupled with the drive system through a control device for switching it on and off.

As soon as the object 1 has left the viewing field of the lens 14, the shutter 30 is closed by means of an appropriate control and the shutter 31 is opened. The light coming from the object 1 and passing through the lens 16 reaches the decoupling lens 23, the lens group 26 and the imaging radiation paths 17.1, 17.2 of the observation device 13, so that the intermediate image 27 thus generated, is deflected and the splitter panels of the radiation splitters 25.1 and 25.2, through the tube lens systems 19.1 and 19.2, reaches the eyepieces 20.1 and 20.2 and the operator now views the object 1 through the lens 16, respectively the sector 2 to be treated.

To initiate the treatment procedure, the laser scan device 15 is started up and the laser radiation 32 generated by it is deflected at the splitter layer of the decoupling device 23, fashioned as a radiation splitter, to the lens 16 and then guided through it scanning over, respectively through the sector 2 of the object 1. The course of the treatment procedure is monitored by the operator through the eyepiece 16.

The device according to the invention makes it possible to observe the object 1 stereoscopically during the preparatory and the evaluative modes and the operator can continue to monitor the treatment procedure through the same eyepieces 20.1, 20.2, which allow the stereoscopic observation during the preparatory and the evaluative modes.

If the relative shifting between object 1 and the device according to the invention is designed in such a fashion, that the device itself remains stationary while the object 1 is moved in direction R, the operator is able to maintain his viewing direction through the eyepieces 20.1, 20.2 also during the transition from the preparatory and evaluative modes to the treatment mode.

This device makes it possible to use a lens 14, or 16, which is matched to the special needs of each purpose, to image object 1 during both operating modes, i.e. to achieve a stereoscopic image with large focal intercept during the preparatory and the evaluative modes on one hand and an image with smaller focal intercept during the treatment mode on the other hand, so that there is an advantageously large distance between the applicable lens and object 1 maintained during the preparatory and the evaluative modes, while a smaller distance is possible during the treatment mode that is bridged by the contact glass.

As has already been explained, the coupling device 22 can be fashioned in various ways.

Figure 5:
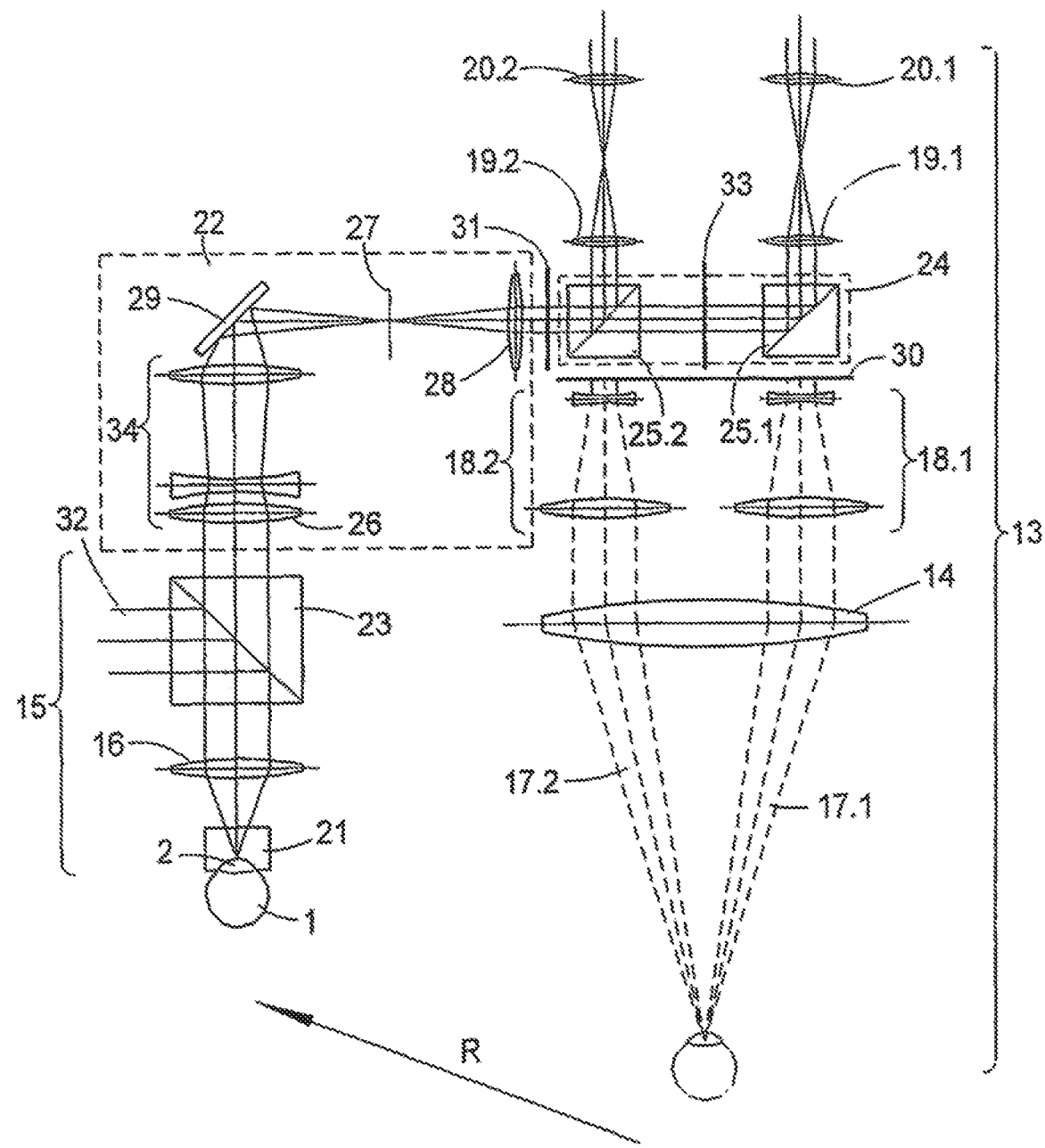
FIG. 5 depicts the device according to the invention with additional optical modules for decoupling of light from the laser scan device and for its coupling into the imaging radiation paths of the observation device, fashioned as a stereoscopic microscope.

In one design variation according to FIG. 5, an additional optical system 34 with variable focal length is placed between the decoupling device 23 and the coupling device 24, which is used to change the imaging scale when showing the sector 2 during the treatment mode.

Figure 6:
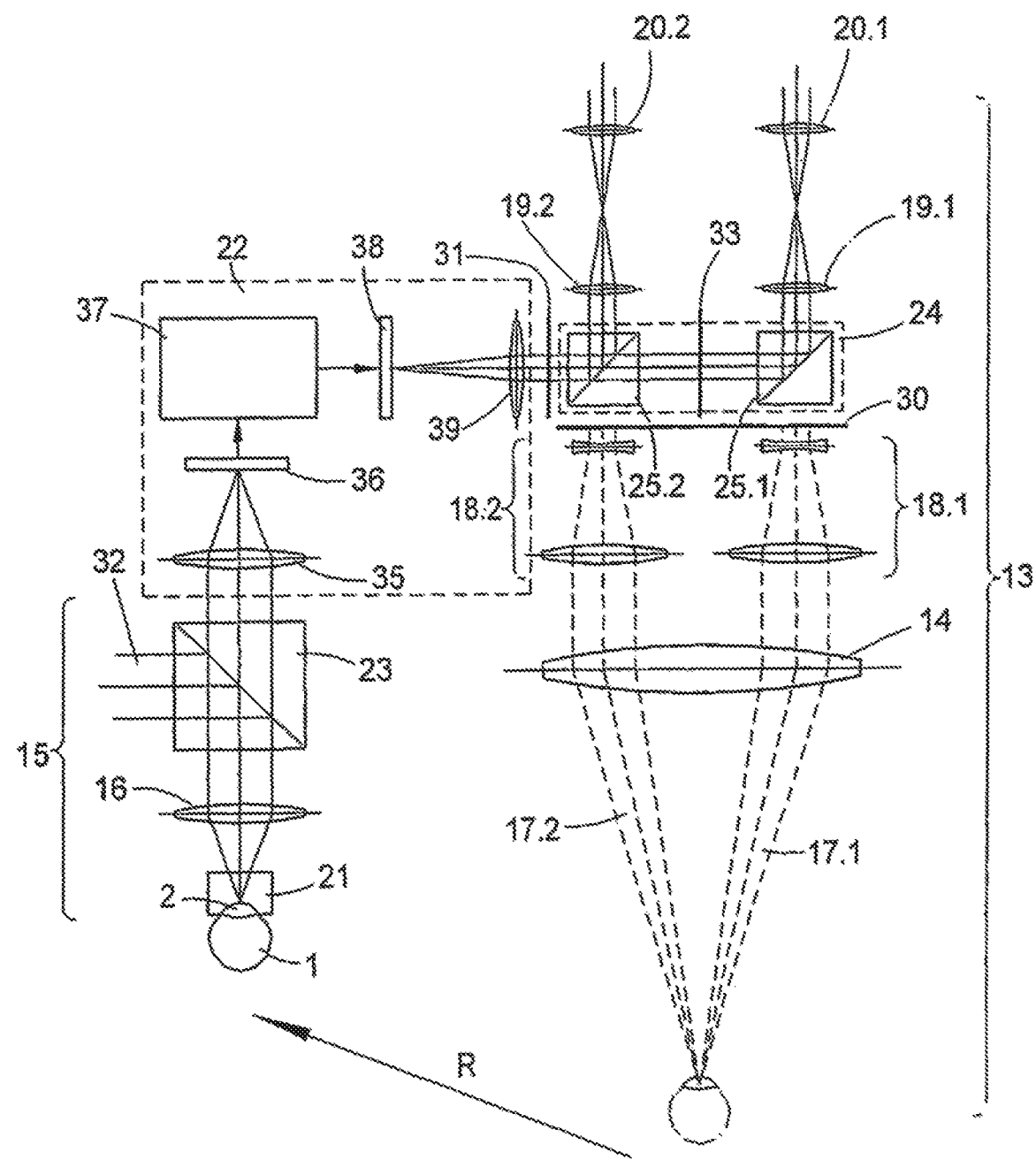
FIG. 6 depicts the device according to the invention with opto-electronic modules for decoupling of light from the laser scan device and for its coupling into the imaging radiation paths of the observation device.

Besides the purely optical devices for transmitting the light from the laser scan device 15 to the observation device 13, the use of opto-electronic modules is possible, as is shown in FIG. 6.

In this case, the object 1, or the sector 2, is imaged first with a video lens 35 on a CCD receiver. In this case, the video lens 35 and CCD receiver 36 are modules of an opto-electronic camera.

As is suggested symbolically in FIG. 6, an image signal processor 37 and an image display device 38 are located downstream from the CCD receiver. For example, the image display device 38 can be fashioned as an LC display.

The image generated on the image display device 38 is coupled into the image radiation paths 17.1, 17.2 via the lens group 39 and the coupling lens 24, which can consist advantageously of two radiation splitters 25.1 and 25.2, as has been shown already.

Figure 7:
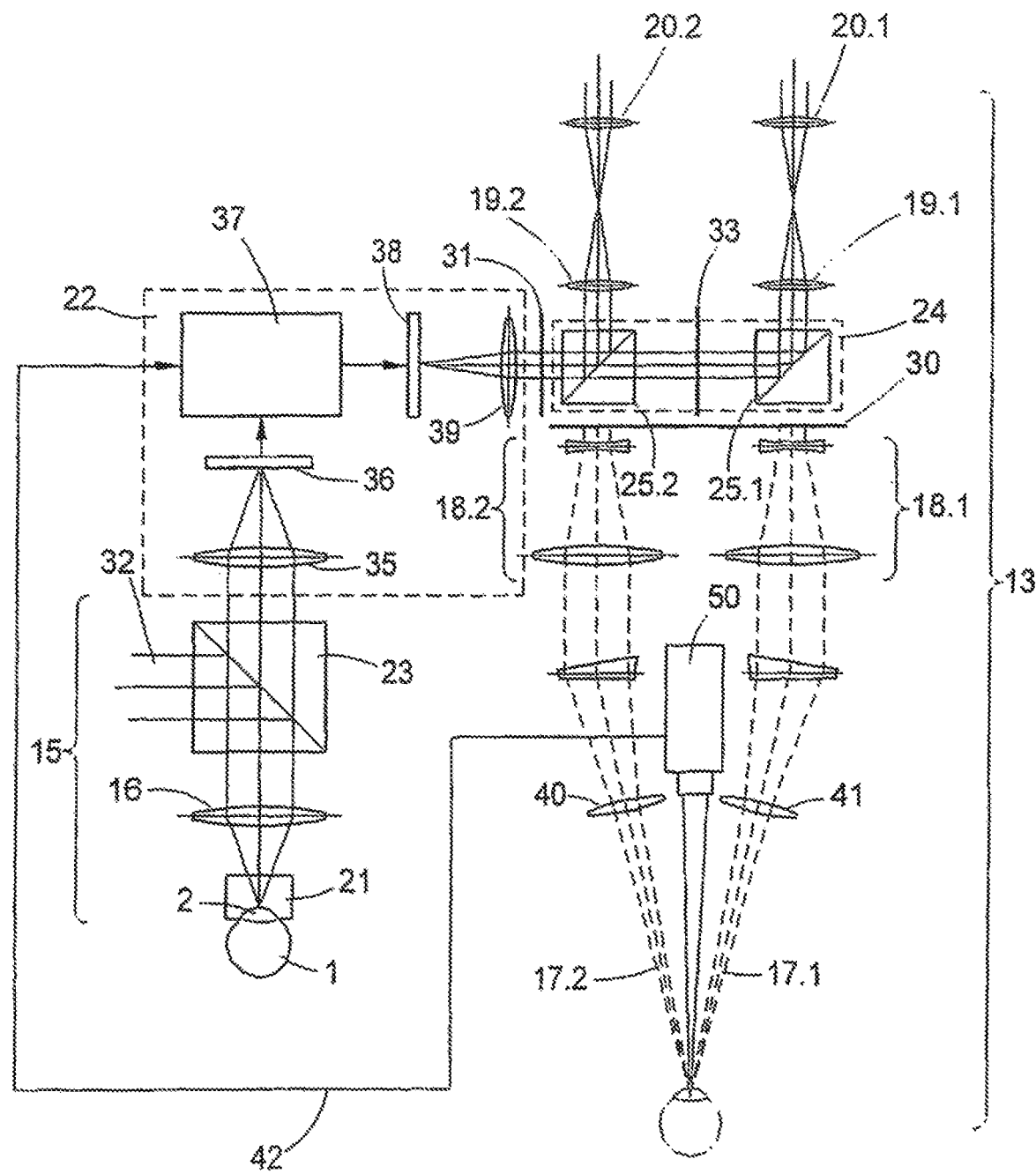
FIG. 7 depicts an embodiment of the device according to the invention, where the observation device is fashioned as a stereoscopic Greenough-type microscope and where a device for obtaining process parameters, properties of the material and/or object dimension is located between the front lenses of this stereoscopic microscope.

In one embodiment of the device according to the invention, shown in FIG. 7, a stereoscopic Greenough-type microscope is provided as the observation device 13. Such a stereoscopic microscope is equipped with a front lens 40, or 41, in each of the observation radiation paths that are tilted toward each other.

Due to the tilting angle toward each other, an open space results between the two imaging radiation paths 17.1, 17.2, which is used, according to the invention, to accommodate a device 50, which is fashioned to acquire:
Process parameters,
Measurement data that characterize the properties of the material the object 1 is made of and/or
Measuring data pertaining to the length to determine the dimensions of the sector 2.

The initial optically determined data are transformed into electronic signals, transmitted via a signal path 42 to the image signal processing device 37, appropriately modified for this embodiment, changed into visible information through image display device 38, and coupled via the coupling optics 24 into one or both imaging radiation paths 17.2, 17.2.

Thereby, during both operating modes, the operator has available not only the images provided through the eyepieces 14 and 16, but also, for example, alpha-numeric information superimposed onto these images.

The capturing and coupling of this information can also be done alone, without showing the object 1.

Figure 8:
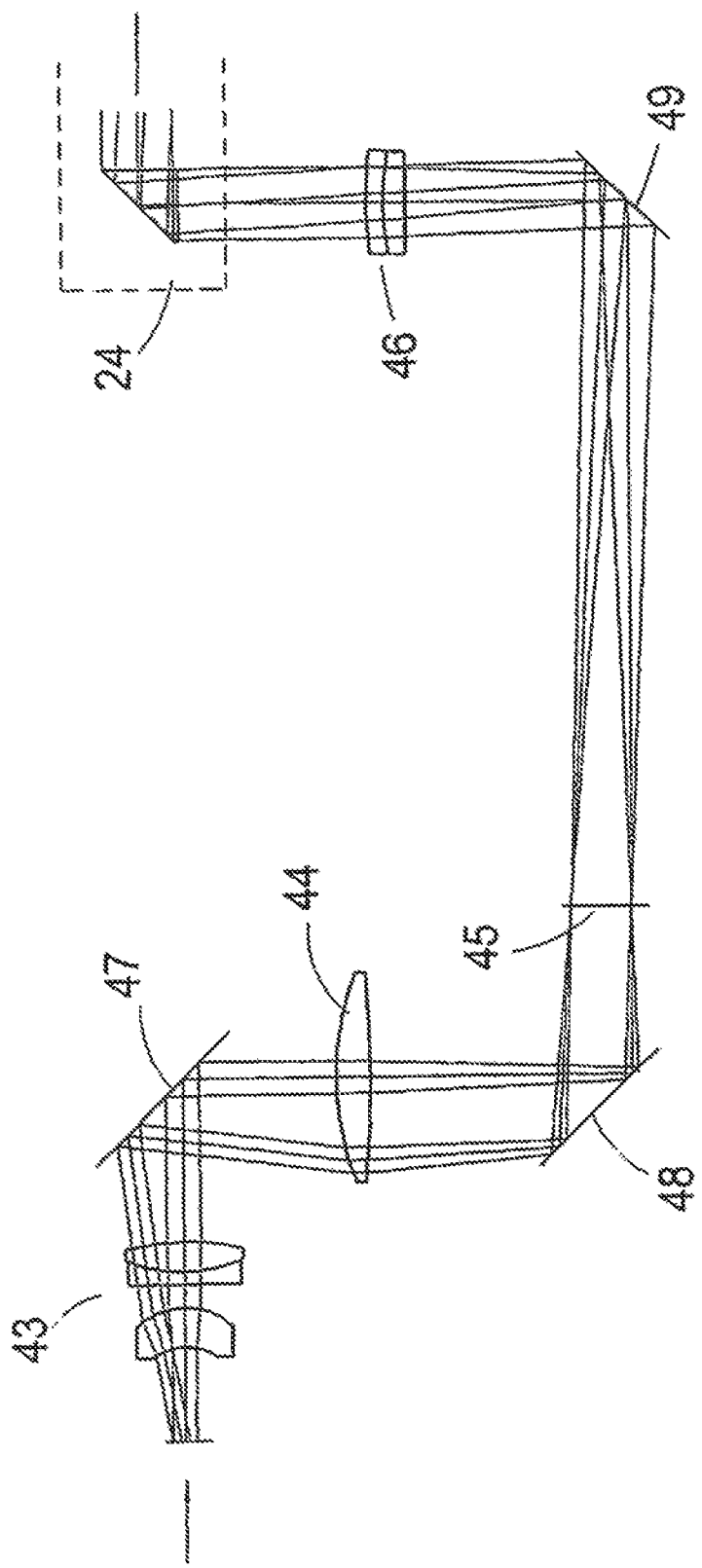
FIG. 8 depicts an actual model of optical modules and their interaction in transmitting light from the laser scan device to the observation device.

FIG. 8 shows in more concrete terms the embodiment of optical modules and their interaction to transmit light from the laser scan device 15 to the observation device 13, largely consisting of:
An optical module 43 and a field lens 44, which combine the light bundles coming from the laser scan device (not pictured here) into an intermediate image 45, and
An optical module 46, which superimposes the intermediate image 45 via the coupling optics 24 into the imaging radiation paths 17.1, 17.2, and thereby into the tube lens systems 18.1, 18.2 (not pictured here) of the observation device 13.

The mirrors 47, 48 and 49 allow matching the radiation path to the given spatial circumstances.

Figure 9:
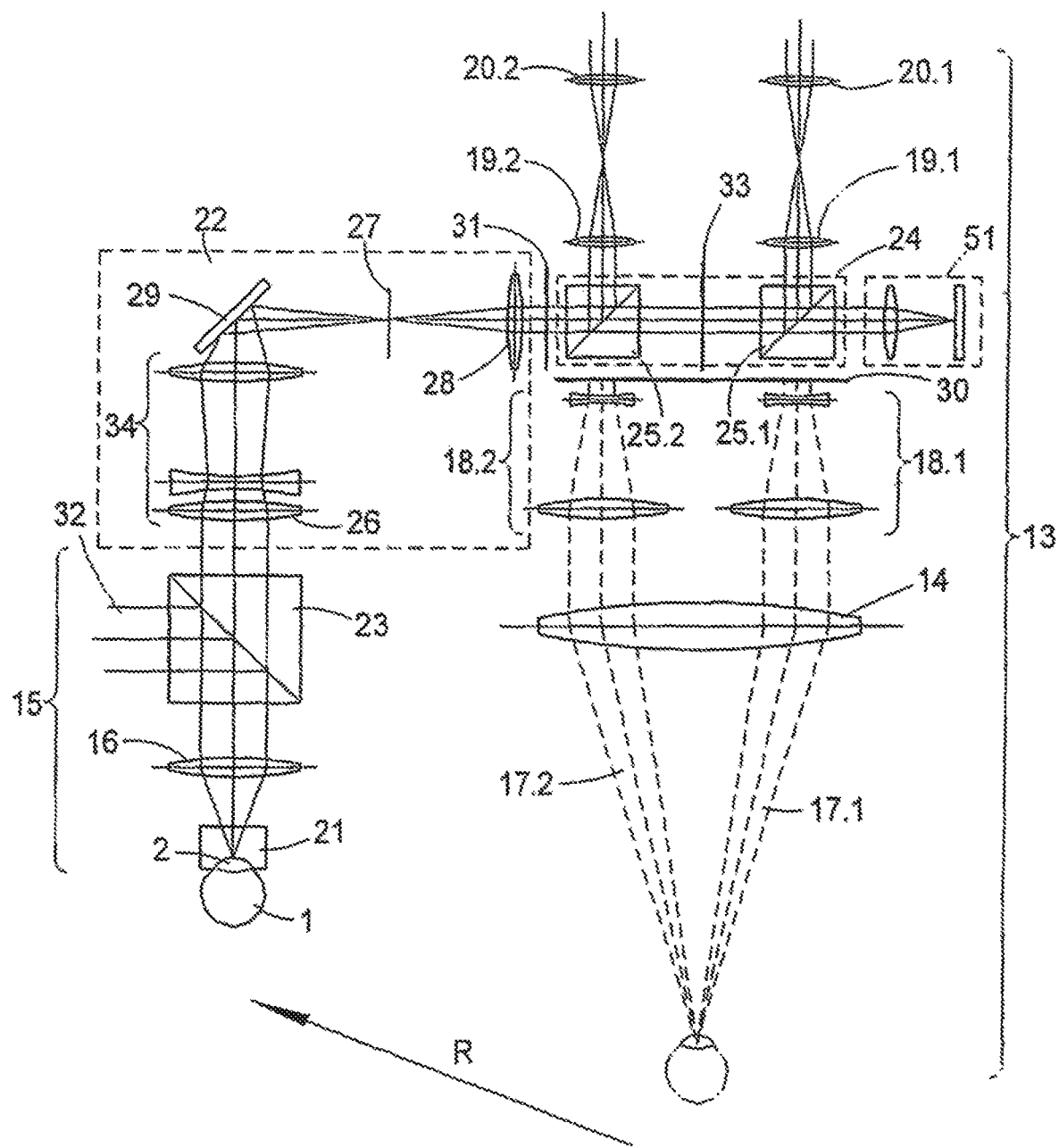
FIG. 9 depicts an embodiment of the device according to the invention, whereby the coupling lens is fashioned as a binocular splitter with decoupling of an imaging radiation path for a CCD camera.

Similar to FIG. 5, FIG. 9 shows an embodiment of the device according to the invention, where the coupling optics 24 is fashioned as a binocular splitter with decoupling of a part of the radiation directed at a CCD camera.

Figure 10:
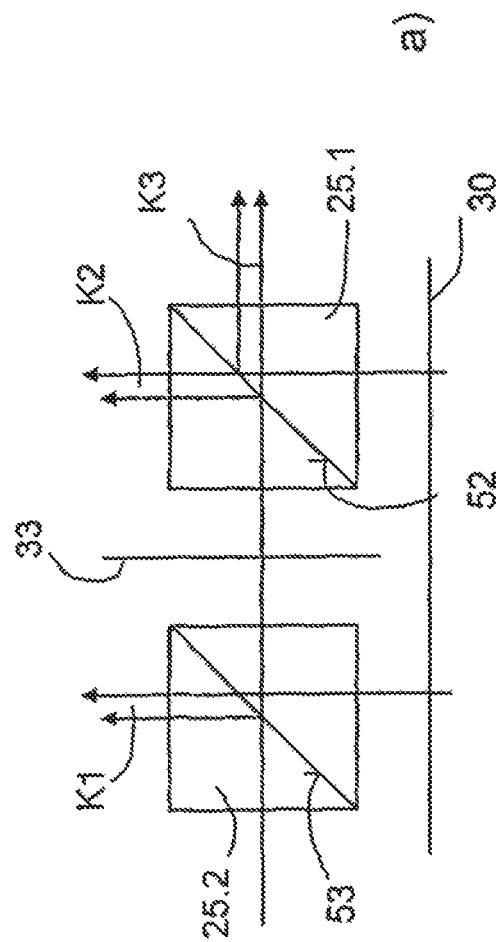
FIG. 10 depicts an example of the binocular splitter from FIG. 9, including three example presets for splitting ratios.

In this embodiment, imaging of the object 1 or of the sector 2 is possible on the CCD camera during the preparatory and the evaluative modes as well as during the treatment mode. The images acquired this way could support the treatment mode through an adjustment process. In FIG. 10, the coupling optics 24 from FIG. 9 is shown as an individual device. It is evident that the light coming from the object 1 is distributed to three channels K1, K2, K3, where channels K1, K2 are assigned to the tube lens systems 19.1 or 19.2 (see FIG. 9) and channel K3 to the CCD camera 51.

Through the appropriate selection of the splitting ratios (transmission/reflection) at the splitter panels 52, 53 of the radiation splitters 25.1 or 25.2, the brightness of the images can be optimized, whereby the optimal brightness of the images of the object 1 acquired during the preparatory and evaluative modes can be different from the brightness desired during the treatment mode.

In this context, example presets T1, T2, T3 are provided in the table following FIG. 10b as examples for splitting ratios.

With the preset T1, images of optimized brightness are achieved during the preparatory and evaluative mode (via the eyepiece 14 or 16). In this case, the transmission is relatively large and the images generated via the channels K1 and K2 are of the same brightness.

The brightness values of the images acquired during the treatment mode (through the eyepiece 16) differ from these. This way, for example, two radiation splitters 25.1 and 25.2 can be used with the same splitting ratios.

With preset T2, the images acquired during the treatment mode are equally bright. With preset T3, the images acquired during the preparatory and evaluative modes have the same brightness as those acquired during the treatment mode. However, different splitting ratios are required at the radiation splitters 25.1 or 25.2.

Depending upon which one of these options is desired, presetting of the splitting ratio does not take place. As a precaution, it must be pointed out that these examples proceed from the assumption of low-loss or loss-free layers. If the absorption by the splitter layers reaches a relevant magnitude, the actual splitting ratios will change slightly.

Figure 11:
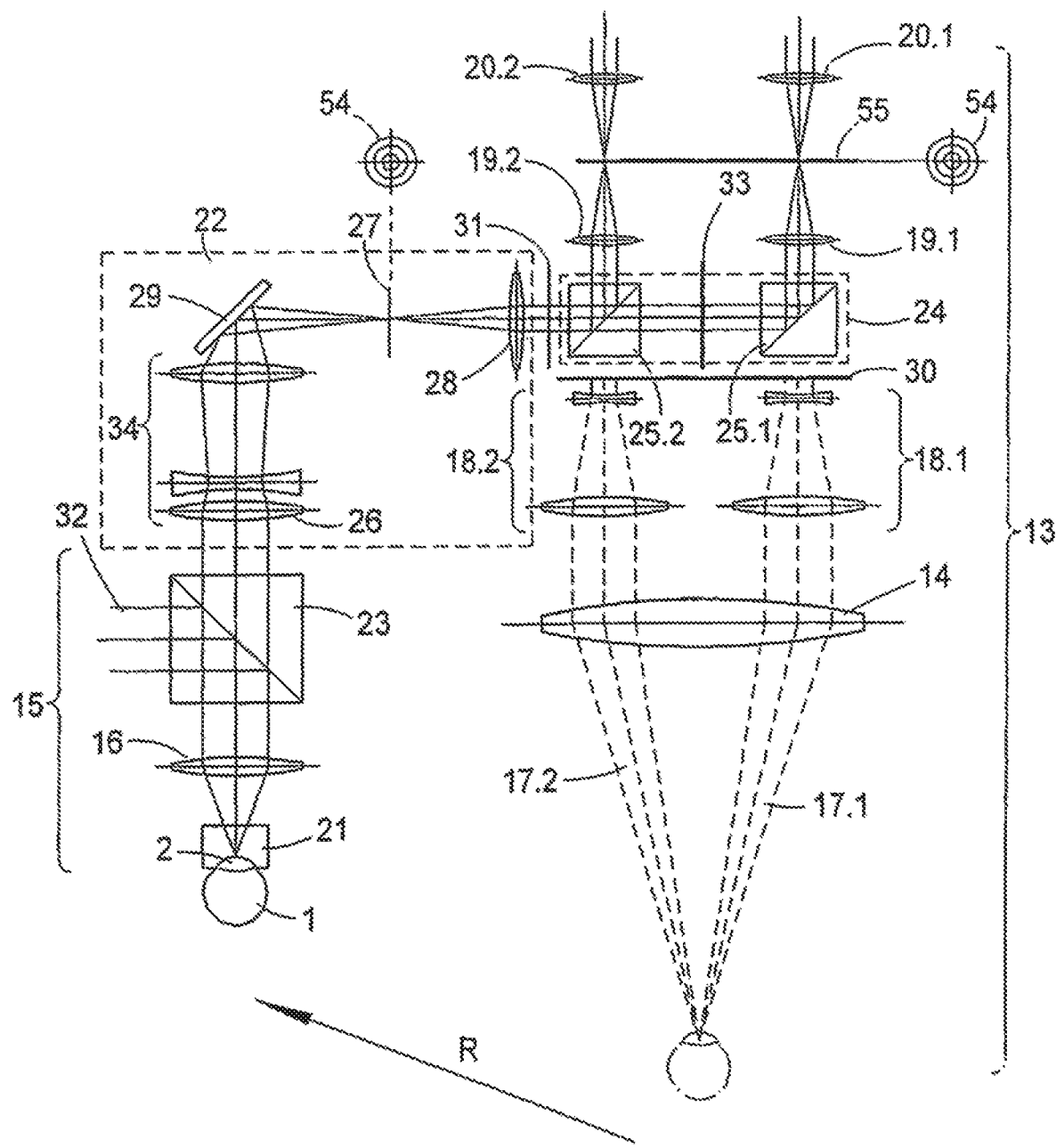
FIG. 11 depicts examples for the location of target markers in intermediate image planes that serve to align the object to be treated relative to the laser scan device.

When operating the device according to the invention, the preparation for the treatment of the object 1, the object 1 is positioned relative to the laser scan device 15. To enable the operating personnel to compare the nominal position with the actual position, it is an advantage to visualize the position of the object 1 relative to a reference point on the device. Such a reference point can be created as a target mark 54 that is mounted to a transparent plate located in an intermediate image plane. Suitable intermediate image locations are shown in FIG. 11 as examples. According to this, the plate with the target mark 54 can be located in the intermediate image 27 of the coupling device 22 or within the intermediate images 55 of the eyepieces 20.1, 20.2.

In addition, the reference point can also be visualized via a display 38 (see FIG. 7). For visualizing the object 1, various realizations are possible. Some objects 1 have a structure, where the characteristic points can be described. In the eye of the patient, the center of the pupil can be chosen as the reference. Another option would be attaching an artificial marker.

As an option, there is the acquisition of the process parameters during the treatment mode, after the object 1 to be treated has been positioned relative to the laser scan device 15. For example, the principle of confocal microscopy for determining the thickness of the cornea can be used, if the object 1 happens to be an eye (pachymetry). Also other parameters can be determined using such a setup, for example the thickness of the epithelium.

Another possibility to acquire process parameters is the use of interferometric detectors. For example, an OCT (optical coherence tomography) can be conducted with the help of interferometric configurations.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

LIST OF REFERENCE TERMS

1—object
2—sector
3—observation device
4—lens
5—radiation path
5.1, 5.2—partial radiation paths
6—radiation splitter
7—splitter system
8—laser radiation
9.1, 9.2—tube lenses
10.1, 10.2—eyepieces
11—lens group
13—observation device
14—lens
15—laser scan device 16—lens
17.1, 17.2—imaging radiation paths
18.1, 18.2—magnification changers
19.1, 19.2—tube lens systems
20.1, 20.2—eyepieces
21—contact glass
22—coupling device
23—decoupling device
24—coupling optics
25.1, 25.2—radiation splitters
26—lens group
27—intermediate image
28—lens group
29—deflection element
30, 31—shutters
32—laser radiation
33—shutter
34—optical system
35—video lens
36—CCD receiver
37—image signal processor device
38—image display device
39—lens group
40, 41—front lenses
42—signal path
43—optical module
44—field lens
45—intermediate image
46—optical module
47, 48, 49—mirrors
50—acquisition device
51—CCD camera
52, 53—splitter layers
54—target mark
55—intermediate image
K1, K2, K3—channels
T1, T2, T3—presets for splitting ratios
R—direction

The invention claimed is:

1. A device for treating an eye using laser radiation, comprising:
an observation device having a first objective lens that images the eye, the first objective lens being configured to image the eye along a first optical path;
a treatment laser source that emits the laser radiation in femtosecond laser pulses that create photodisruption in tissues of the eye;
a laser scan device including a second objective lens that images the eye and through which the laser radiation is guided to scan through a sector within the eye that is intended to be treated; the second objective lens being configured to image the eye along a second optical path;
wherein the first objective lens and the second objective lens are different from each other in a size of a segment presented for observation in the images and/or in terms of a focal intercept of the first objective lens and the second objective lens;
further wherein, the first objective lens and the second objective lens are shiftable to image the eye along the first optical path and the second optical path; and
further wherein during a first operating mode, the eye is in focus via the first objective lens, and during a second operating mode, the eye is in focus via the second objective lens.

2. The device according to claim 1, further comprising:
a first optical decoupling device located within a radiation path of the laser scan device, the first optical decoupling device comprising a radiation splitter for light coming from the sector of the eye and passing through the second lens;
a second optical coupling device for decoupled light located within the radiation path of the observation device; and
optical or opto-electronic modules for transmission of the light to the optical decoupling device.

3. The device according to claim 2, further comprising:
a structure selected from a group consisting of
a shutter between the second lens and the optical coupling device, which blocks light coming from the first lens during the second operating mode,
a shutter provided between the first lens and the optical coupling device, which blocks light coming from the second lens during the first operating mode, or
both of the foregoing.

4. The device according to claim 1, wherein the observation device includes a stereoscopic microscope comprising:
the first lens;
two separate imaging radiation paths, allowing stereoscopic imaging; and
located in each of the two imaging radiation paths,
a magnification changer for presetting different magnifications during the first operating mode;
a tube lens system;
an eyepiece; and
an optical coupling device having a first radiation splitter and a second radiation splitter, wherein the first radiation splitter is located within the imaging radiation path and the second radiation splitter is located between the magnification changer and the tube lens system.

5. The device according to claim 1, further comprising optical modules that comprise:
a first lens group to combine light bundles coming through the second lens into an intermediate image;
a second lens group to display the intermediate image into the imaging radiation path of the observation device; and
optical elements to deflect the radiation, fold the radiation or to deflect and fold the radiation.

6. The device according to claim 1, further comprising opto-electronic modules to transmit the light from the laser scan device to the observation device, wherein
imaging of the eye is done using a second eyepiece via a video lens to a CCD receiver;
further comprising an image signal processor device and an image display device downstream from the CCD receiver; and
means for coupling the image shown on the image display device into the imaging radiation paths of the observation device, whereby
the image generated during the second operating mode by the second lens is visible through the eyepieces.

7. The device according to claim 1, further comprising an acquisition device for acquiring:
process parameters concerning the treatment procedure,
data concerning the properties of the material making up the eye, or
data concerning the dimensions of the eye.

8. A device for treating an eye using laser radiation, comprising:
an observation device having a first objective lens that images the eye, the first objective lens being configured to image the eye along a first optical path;

a treatment laser source that emits the laser radiation in femtosecond laser pulses that create photodisruption in tissues of the eye;

a laser scan device including a second objective lens that images the eye and through which the laser radiation is guided so as to scan through a sector within the eye that is intended to be treated; the second objective lens being configured to image the eye along a second optical path; a treatment laser source that emits the laser radiation in femtosecond laser pulses that create photodisruption in tissues of the eye;

a laser scan device including a second objective lens that images the eye and through which the laser radiation is guided so as to scan through a sector within the eye that is intended to be treated; the second objective lens being configured to image the eye along a second optical path;

wherein the first objective lens and the second objective lens are different from each other in a size of a segment presented for observation in the images and/or in terms of their focal intercept;

further wherein, the first objective lens and the second objective lens are shiftable to image the eye in a first operating mode-along the first optical path and to image the eye in a second operating mode-along-the-second optical path; and further wherein during the first operating mode, the eye is in focus via the first objective lens, and during the second operating mode, the eye is in focus via the second objective lens.

9. The device according to claim 8, further comprising:
an optical decoupling device located within a radiation path of the laser scan device, the optical decoupling device comprising a radiation splitter for light coming from the sector of the eye and passing through the second lens;
an optical coupling device for decoupled light located within the radiation path of the observation device; and
optical or opto-electronic modules for transmission of the light to the optical decoupling device.

10. The device according to claim 9, further comprising:
a structure selected from a group consisting of a shutter between the second lens and the optical coupling device, which blocks light coming from the first lens during the second operating mode;
a shutter provided between the first lens and the optical coupling device, which blocks light coming from the second lens during the first operating mode; or both of the foregoing.

11. The device according to claim 8, wherein the observation device includes a stereoscopic microscope comprising:
the first lens;
two separate imaging radiation paths, allowing stereoscopic imaging; and
located in each of the two imaging radiation paths;
a magnification changer for presetting different magnifications during the first operating mode;
a tube lens system;
an eyepiece; and
an optical coupling device having a first radiation splitter and a second radiation splitter, wherein the first radiation splitter is located within the imaging radiation path and the second radiation splitter is located between the magnification changer and the tube lens system.

12. The device according to claim 8, further comprising optical modules that comprise:
a first lens group to combine light bundles coming through the second lens into an intermediate image;
a second lens group to display the intermediate image into the imaging radiation path of the observation device; and
optical elements to deflect the radiation, fold the radiation or to deflect and fold the radiation.

13. The device according to claim 8, further comprising opto-electronic modules to transmit the light from the laser scan device to the observation device, wherein:
imaging of the eye is done using a second eyepiece via a video lens to a CCD receiver;
further comprising an image signal processor device and an image display device downstream from the CCD receiver; and
means for coupling the image shown on the image display device into the imaging radiation paths of the observation device, whereby
the image generated during the second operating mode by the second lens is visible through the eyepieces.

14. The device according to claim 8, further comprising an acquisition device for acquiring:
process parameters concerning the treatment procedure,
data concerning the properties of the material making up the eye, or
data concerning the dimensions of the eye.

15. A method for treating an eye using laser radiation, comprising:
observing the eye via an observation device having a first objective lens that images the eye, the first objective lens being configured to image the eye along a first optical path wherein the first objective lens and the second objective lens are different from each other in a size of a segment presented for observation in the images and/or in terms of their focal intercept;
treating the eye by application of a treatment laser source that emits the laser radiation in femtosecond laser pulses that create photodisruption in tissues of the eye;
guiding the laser radiation through a laser scan device including a second objective lens that images the eye to scan through a sector within the eye that is intended to be treated wherein the second objective lens is configured to image the eye along a second optical path;
shifting the first objective lens and the second objective lens to image the eye along the first optical path and the second optical path; and
operating in a first operating mode, wherein the eye is in focus via the first objective lens, and operating in a second operating mode, wherein the eye is in focus via the second objective lens.

16. The method according to claim 15, further comprising:
optically decoupling radiation within a radiation path of the laser scan device by application of a first optical decoupling device comprising a radiation splitter for light coming from the sector of the eye and passing through the second lens;
optically decoupling radiation located within the radiation path of the observation device by application of a second optical coupling device for decoupled light located within the radiation path of the observation device; and
utilizing optical or opto-electronic modules for transmission of the light to the first optical decoupling device, the second optical decoupling device or both.

17. The method according to claim 16, further comprising:
utilizing a structure selected from a group consisting of
a shutter between the second lens and the optical coupling device, to block light coming from the first lens during the second operating mode,
a shutter provided between the first lens and the optical coupling device, block light coming from the second lens during the first operating mode, or
both of the foregoing.

18. The method according to claim 15, further comprising:
directing light bundles coming through the second lens to a first lens group thereby combining the light bundles coming through the second lens into an intermediate image;
further directing the light bundles to a second lens group thereby displaying the intermediate image into the imaging radiation path of the observation device; and
further directing the light bundles to optical elements that deflect the radiation, fold the radiation or that deflect and fold the radiation.

19. The method according to claim 15, further comprising:
transmitting the light from the laser scan device to the observation device by way of opto-electronic modules;
imaging the eye by using a second eyepiece via a video lens to a CCD receiver;
processing an image signal with a processor device and displaying an image on a display device downstream from the CCD receiver; and
coupling the image shown on the image display device into the imaging radiation paths of the observation device, whereby the image generated during the second operating mode by the second lens is visible through the eyepieces.

20. The method according to claim 15, further comprising acquiring:
process parameters concerning the treatment procedure of the eye;
data concerning the properties of the material making up the eye; or
data concerning the dimensions by application of an acquisition device.

* * * * *